United States Patent [19]

Van der Knaap

[11] Patent Number: Plant 6,341

[45] Date of Patent: Oct. 18, 1988

[54] CHRYSANTHEMUM PLANT NAMED MONEYMAKER

[75] Inventor: Jacques C. M. Van der Knaap, De Lier, Netherlands

[73] Assignee: Fides Beheer B.V., De Lier, Netherlands

[21] Appl. No.: 532,890

[22] Filed: Nov. 20, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A chrysanthemum plant named Moneymaker particularly characterized by its anemone capitulum type and flat capitulum form; light pink ray floret color, and by its light pink mature petaloids which form around the disc florets.

1 Drawing Sheet

The present invention comprises a new and distinct cultivar of Chrysanthemum, botanically known as *Chrysanthemum morifolium,* Ramat., and referred to by the cultivar name Moneymaker.

Moneymaker is a product of a planned breeding program which had the objective of creating new chrysanthemum cultivars for cut spray programs having anemone capitulum type, light pink ray floret color, eight weeks response and the ability to produce commercially acceptable quality in year around cut mum programs. Such traits in combination were not present in previously available commercial cultivars.

Moneymaker was originated by applicant from a hybridization made in a controlled breeding program in De Lier, The Netherlands in 1982. The female parent was the cultivar Cherub. The male parent of Moneymaker was the cultivar Yvonne.

Moneymaker was discovered and selected by applicant as one flowering plant within the progeny of the stated parentage in June of 1983 in a controlled environment in De Lier, The Netherlands.

The first act of asexual reproduction of Moneymaker was accomplished when vegetative cuttings were taken from the initial selection in July of 1983 in a controlled environment in De Lier, The Netherlands by a technician working under formulations established and supervised by applicant. Horticultural examination of selected units initiated in October of 1983 has demonstrated that the combination of characteristics as herein disclosed for Moneymaker are firmly fixed and are retained through successive generations of asexual reproduction.

Moneymaker has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial practice.

The following traits have been repeatedly observed and are determined to be basic characteristics of Moneymaker, which, in combination, distinguish this chrysanthemum as a new and distinct cultivar:

1. Flat capitulum form.
2. Anemone capitulum type.
3. Pink ray floret color.

4. Diameter across the face of the capitulum of 45–50 mm.
5. Pink (immature) to pinkish white (mature) petaloids formed around the disc florets.

Of the many commercial cultivars known to the present inventor, the most similar in comparison to Moneymaker is the cultivar Remember. In comparison to Remember, Moneymaker has relatively smaller flowers, a different pink flower tone, and an earlier response. The flower center and flower type of Moneymaker are similar to those same characteristics of Remember.

The accompanying color photographic drawing shows in front view typical inflorescence and foliage characteristics of Moneymaker, with colors being as nearly true as possible with illustrations of this type.

In the following description, color references are made to The Royal Horticultural Society Colour Chart. The color values were determined between 11:00 a.m. and 12:00 noon in September under natural daylight at De Lier, The Netherlands.

Classification:

*Botanical.*—*Chrysanthemum morifolium,* Ramat., cv. Moneymaker.

*Commercial.*—Cut anemone spray.

INFLORESCENCE

A. Capitulum:

*Form.*—Flat.

*Type.*—Anemone.

*Diameter across face.*—45–50 mm.

B. Corolla of ray florets:

*Color (general tonality from a distance of three meters).*—Light pink.

*Color (upper surface).*—36D, fading to near white.

*Color (under surface).*—Somewhat lighter than 36D.

C. Corolla of disc florets:

*Color.*—Pink-orange (immature) 27B maturing to color36D of ray florets. Petaloids around disc florets are 36D, color of ray florets; disc florets range from 27B to 36D.

D. Reproductive organs:

*Androecium.*—Present only in disc florets; numerous.

*Gynoecium.*—Present in both ray and disc florets; numerous.

PLANT

A. General appearance:

*Height.*—90 cm.

B. Foliage:

*Color* (*upper surface*).—137A.

*Color* (*under surface*).—137B.

*Shape.*—Deeply serrated.

I claim:

1. A new and distinct cultivar of chrysanthemum plant named Moneymaker, as described and illustrated, and particularly characterized by its anemone capitulum type and flat capitulum form; light pink ray floret color, and by its light pink mature petaloids which form around the disc florets.

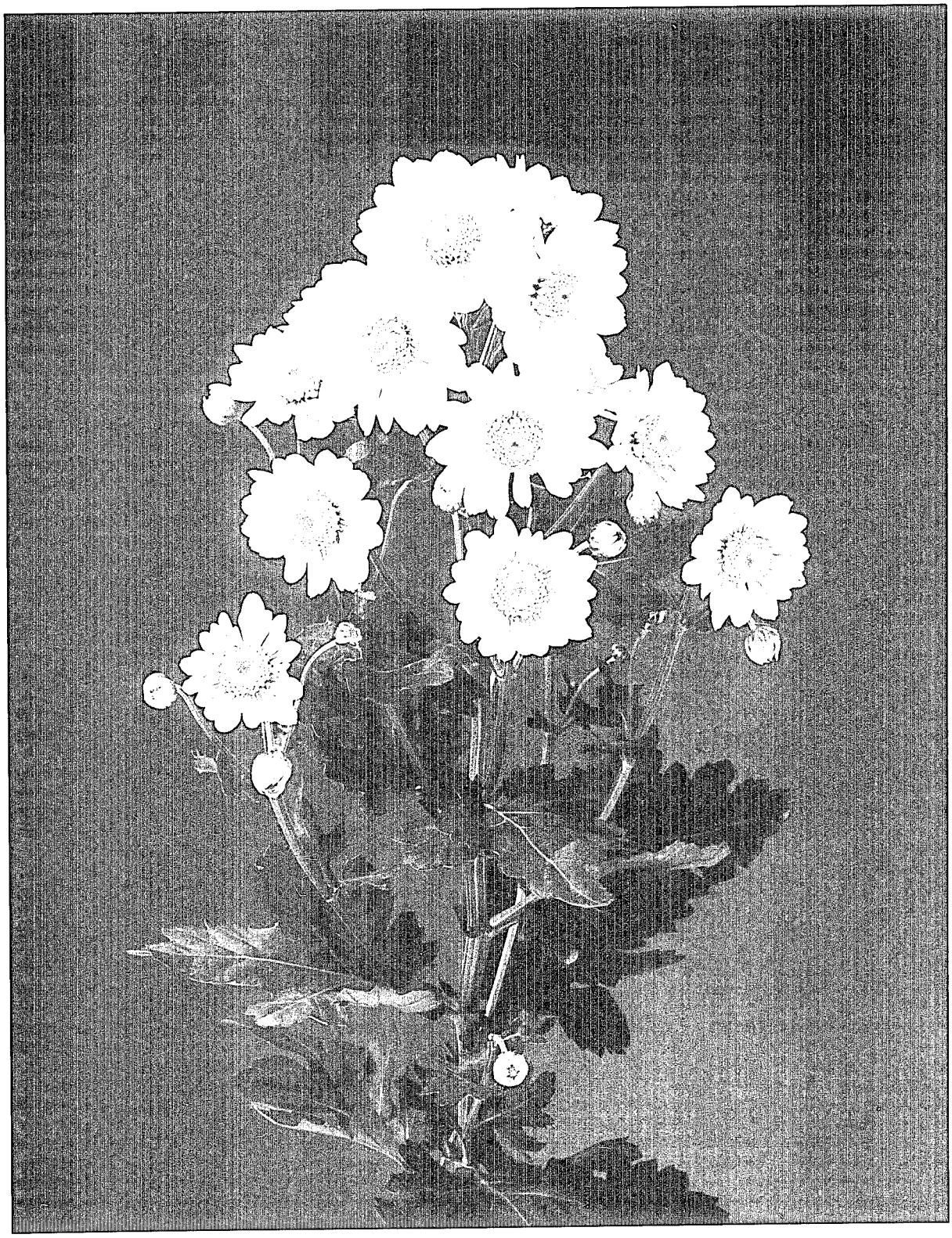

* * * * *